United States Patent [19]

Ozutsumi et al.

[11] 3,930,672

[45] Jan. 6, 1976

[54] PRESSURE-SENSITIVE COPYING PAPER CONTAINING LACTONE COMPOUNDS DERIVED FROM PYRIDINE-CARBOXYLIC ACID

[75] Inventors: Minoru Ozutsumi; Yoshihide Miyazawa; Susumu Suzuka, all of Tokyo; Sadao Ishige, Kanagawa; Keiso Saeki; Akio Watanabe, both of Shizuoka, all of Japan

[73] Assignees: Hodogaya Chemical Co., Ltd., Tokyo; Fuji Photo Film Co., Ltd., Minami-ashigara, both of Japan

[22] Filed: Mar. 25, 1974

[21] Appl. No.: 454,527

[30] Foreign Application Priority Data
Mar. 23, 1973 Japan.................................. 48-32719

[52] U.S. Cl. ............... 282/27.5; 427/151; 427/152; 428/323; 428/411; 260/295; 260/335
[51] Int. Cl.². B41M 5/12; B41M 5/16; B41M 5/22
[58] Field of Search ....... 117/36.2, 36.7, 36.8, 36.9; 260/295 B, 295 T, 295 R

[56] References Cited
UNITED STATES PATENTS

| | | | |
|---|---|---|---|
| 3,669,710 | 6/1972 | Kimura et al. | 117/36.2 |
| 3,725,416 | 4/1973 | Yamamoto et al. | 260/293.58 |
| 3,730,754 | 5/1973 | Farber et al. | 117/36.2 |
| 3,775,424 | 11/1973 | Farber | 260/295 B |
| 3,787,325 | 1/1974 | Hoover | 260/287 R |

*Primary Examiner*—P. E. Willis, Jr.
*Attorney, Agent, or Firm*—Sughrue, Rothwell, Mion, Zinn & Macpeak

[57] ABSTRACT

A pressure-sensitive copying paper comprising an adsorbent solid acid and a microencapsulated color former capable of forming a distinct color when reacted with the adsorbent acid coated on the same or a different surface of a support or supports, the microencapsulated color former being at least one lactone compound derived from a pyridine-carboxylic acid represented by the formula

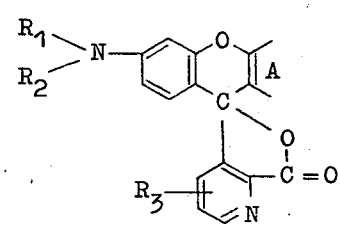

or

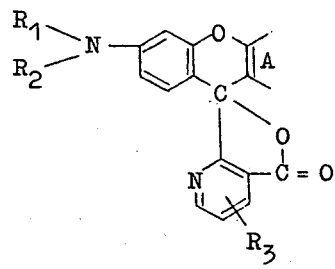

(I)

or a mixture thereof, wherein $R_1$, $R_2$, $R_3$ and the partial structure

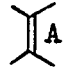

are as defined hereinafter, is disclosed.

7 Claims, No Drawings

PRESSURE-SENSITIVE COPYING PAPER CONTAINING LACTONE COMPOUNDS DERIVED FROM PYRIDINE-CARBOXYLIC ACID

BACKGROUND OF THE INVENTION

1. Field of the Invention

This invention relates to a pressure-sensitive copying paper using as a color former a pyridine-carboxylic acid lactone represented by the formula

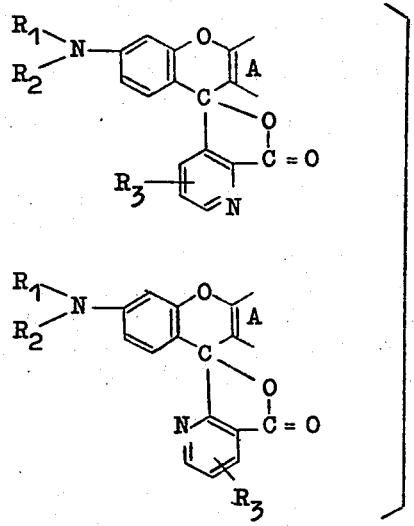

or a mixture thereof, wherein $R_1$ represents a hydrogen atom, a lower alkyl group or a benzyl group; $R_2$ represents a lower alkyl group, a benzyl group or a substituted or unsubstituted phenyl group wherein the substituent is a lower alkyl group or a halogen atom; $R_3$ represents a hydrogen atom, a lower alkyl group, a halogen atom or a phenyl group; and

represents

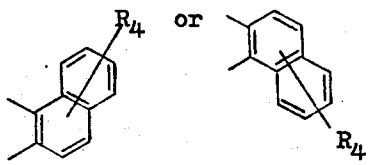

wherein $R_4$ represents a hydrogen atom, a lower alkyl group, a lower alkoxy group, a halogen atom, an amino, mono-lower alkylamino, di-lower alkylamino, mono-benzylamino, dibenzylamino, N-lower alkyl-N-benzylamino, anilino, N-lower alkylanilino or -NHCO-X group wherein X represents a lower alkyl, lower alkenyl or a substituted or unsubstituted styryl, phenyl or naphthyl group, the substituent being a lower alkyl, lower alkoxy, di-lower alkylamino, hydroxy or nitro group or a halogen atom, wherein the lower alkyl, alkoxy and alkenyl groups have 1 to 5 carbon atoms.

2. Description of the Prior Art

In general, pressure-sensitive copying paper comprises the combination of an upper sheet paper (or transfer sheet) having coated on the back surface thereof minute microcapsules containing dissolved therein an electron donative substantially colorless organic compound capable of undergoing color reaction, i.e., color former, and a lower sheet paper (or receiving sheet) having coated on the surface thereof a color developer. When these two coated surfaces are brought into contact with each other and a localized pressure is applied to the assembly by handwriting or typewriting, microcapsules located at the pressure-applied area rupture and the organic color former contained in the organic solvent comes into contact with the color developer to form color.

Pressure-sensitive copying paper systems comprising the aforesaid transfer sheet and a receiving sheet and an intermediate sheet are also known. In these systems the middle sheet is usually coated, on opposite surfaces, with a layer of microcapsules containing a color former solution and with a layer of a solid acid and a binder, respectively. Another type of pressure-sensitive copying system is a recording sheet which can be prepared by applying the above described microcapsules and the adsorbent solid acid on the same surface of a support.

As the color developer, there are active clay substances such as acid clay, attapulgite, zeolite, bentonite; solid organic acids such as succinic acid, tannic acid, benzoic acid; and acidic polymers such as phenol-formalin polymer, phenol-acetylene polymer, residual acid group-containing styrene-maleic anhydride polymer, salicylic acid-formalin polymer.

As the organic solvent for dissolving the color former, there are, such as ethylene glycol, chlorobenzenes, diphenyl chloride, diethyl phthalate, trioctyl phosphate, dibenzyl benzene, dibenzyl toluene, alkyl-naphthalenes and naphthylalkyl alcohols.

SUMMARY OF THE INVENTION

As a result of detailed investigations on the color former for pressure-sensitive copying paper, the present inventors have discovered that there can be obtained a pressure-sensitive copying paper capable of forming an orange, red, purple, blue, green or a like color by using as a color former a novel pyridine-carboxylic acid lactone represented by the above formula (I), and that there can be obtained a pressure-sensitive copying paper capable of forming optional desired color by using the novel color former in combination with a known color former or formers.

DETAILED DESCRIPTION OF THE INVENTION

Compounds represented by the formula (I) which can be used in the present invention are generally excellent in light resistance after color formation, the lactone ring of which is somewhat likely to be cleaved, and capable of forming a deep color when contacted even with organic acids containing a carboxyl group or a phenolic hydroxyl group which are relatively poor in capability of developing color as well as active clay substances in comparison with fluoran containing compounds as disclosed in Japanese Laid-Open Pat. Publication No. 4662/1972 and Japanese Pat. Publication No. 3695/1973.

The lactone color formers of pyridine-carboxylic acid used for pressure-sensitive copying papers of the present invention and the starting material, pyridine-carboxylic acids can be prepared as follows.

1. Preparation of Pyridine-Carboxylic Acid

About 1 mole of quinolinic anhydride represented by the formula

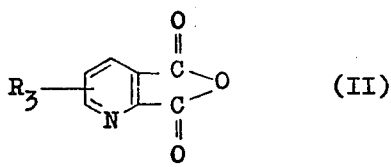
(II)

wherein $R_3$ is as defined in the formula (I) is reacted with about 0.9 to 2 moles of aniline represented by the formula

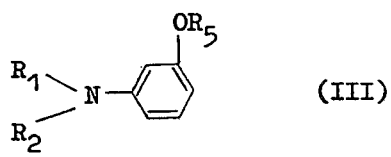
(III)

wherein $R_1$ and $R_2$ are as defined in the formula (I) and $R_5$ represents a hydrogen atom or a lower alkyl group in about 0.5 to 2.5 l of a volatile organic inert solvent such as carbon disulfide, tetrachloroethane, benzene, a chlorobenzene, a nitrobenzene and the like using about 1 to 3 moles of a Friedel-Crafts catalyst such as zinc chloride, aluminum chloride and the like at a temperature of from 10° to 110°C for a period of 1 to 9 hours. The reaction mixture is cooled to room temperature and the inert organic solvent is removed by decantation. The resulting reaction product is poured into ice-water or cold dilute aqueous hydrochloric acid to hydrolyze the catalyst. The precipitated solid is filtered, washed successively with water and benzene and dried. Alternatively, after cooling the reaction mixture as above, the reaction mixture is poured into about 2 to 6 l of ice-water to hydrolyze the catalyst. The same inert organic solvent as used above is then added to the resulting aqueous solution to transfer the reaction product to the solvent layer. The solvent layer is recovered by separation and the solvent is distilled off. There is obtained an isomer mixture comprising 2-benzoyl-pyridine-carboxylic acid-(3) and 3-benzyol-pyridine-carboxylic acid-(2) represented by the formula

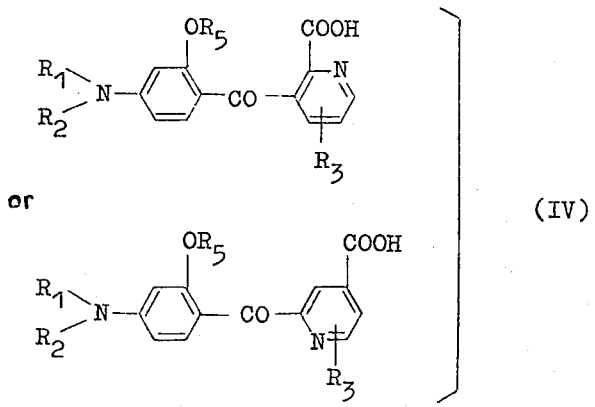
(IV)

wherein $R_1$, $R_2$ and $R_3$ are as defined in the formula (I) and $R_5$ is as defined in the formula (III), respectively, as crystals. If necessary, the above obtained isomer mixture can be separated into each isomer in high purity, i.e., 2-benzoyl-pyridine-carboxylic acid-(3) and 3-benzoyl-pyridine-carboxylic acid-(2), or benzoyl-pyridine-carboxylic acids in which two isomers are present in various proportions can be obtained by (1) dissolving the isomer mixture as above obtained in dilute aqueous sodium hydroxide, carefully adding dilute aqueous hydrochloric acid to the resulting solution in small portions and then recovering each of solids which precipitates due to the difference in pH of the solution or (2) repeatedly recrystallizing the reaction product using a mixture of a less polar solvent such as benzene, toluene and the like and a polar solvent such as methanol, butanol and the like, or a combination of (1) and (2) above.

2. Preparation of Lactone Color Former of Pyridine-Carboxylic Acid Represented by the Formula (I)

(1) About 1 mole of the above obtained 2-benzoyl-pyridine-carboxylic acid-(3), 3-benzoyl-pyridine-carboxylic acid-(2) or a mixture thereof is reacted with about 1 to 1.5 moles of a naphthalene compound represented by the formula

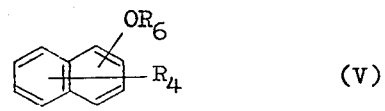
(V)

wherein $R_4$ is as defined in the formula (I) wherein $R_4$ cannot be positioned at 1 or 2, and $R_6$ represents a hydrogen atom or a lower alkyl group, said group $-OR_6$ being positioned at 1 or 2, in about 3 to 30 moles of concentrated sulfuric acid or polyphosphoric acid at a temperature of from about 30° to 130°C for about 2 to 10 hours. The reaction mixture is cooled to room temperature and the reaction product is poured into ice-water. The resulting solution is then made weakly acidic or neutral with dilute aqueous sodium hydroxide. Benzene or toluene is added to the solution followed by stirring to transfer any unreacted naphthalene compound to the benzene or toluene layer which is then removed by separation. The residual aqueous layer is adjusted to a pH of 11 to 12 with dilute aqueous sodium hydroxide. The precipitated solid is collected by filtration, washed successively with water and a small amount of petroleum ether or an alcohol and dried to give a substantially colorless or slightly colored lactone color former of pyridine-carboxylic acid represented by the formula (I) in high yield. Alternatively, the above residual aqueous layer is adjusted to a pH of 11 to 12 with dilute aqueous sodium hydroxide, and benzene or toluene is added thereto followed by stirring to transfer a lactone color former of pyridine-carboxylic acid to the benzene or toluene layer, which is then recovered by separation. Benzene or toluene is then distilled off from the benzene or toluene layer. The residue is washed successively with water and a small amount of an alcohol, petroleum ether or ligroin and dried to give a substantially colorless or slightly colored lactone color former of pyridine-carboxylic acid represented by the formula (I) in high yield. Or else, the reaction product obtained in the above reaction is poured into ice-water, and the resulting aqueous solution is adjusted to a pH of 11 to 12 with dilute aqueous sodium hydroxide. Benzene or toluene is added thereto followed by stirring to transfer the lactone color former of pyridine-carboxylic acid to the benzene or toluene layer. The benzene or toluene layer is recovered by separation and benzene or toluene is distilled off therefrom. The residue is then washed successively with water and a small amount of an alcohol, petroleum ether or ligroin and dried to give a substantially colorless or slightly colored lactone color former of pyridine-carboxylic acid represented by the formula (I).

(2) Pyridine-carboxylic acid lactones represented by the formula (I) wherein $R_4$ is a group —NH—CO—X can be prepared from those lactones in which $R_4$ is an amino group as follows.

About 1 mole of the above obtained pyridine-carboxylic acid lactone of the formula (I) wherein $R_4$ is an amino group is reacted with about 1 to 1.5 moles of an acid halide represented by the formula

$$X - CO - Y \qquad (VI)$$

wherein X is as defined in the formula (I) and Y represents a halogen atom in about 0.3 to 1 l of a volatile inert organic solvent such as chloroform, benzene, toluene, a chlorobenzene and the like in the presence of about 1 to 1.5 moles of an acid acceptor such as triethylamine, pyridine, sodium hydrogen-carbonate and the like at a temperature of about 40° to 110°C for about 2 to 8 hours. The reaction product is cooled to room temperature, and washed with water followed by distilling off the volatile inert organic solvent. The resulting residue is washed successively with water and a small amount of an alcohol, petroleum ether or ligroin and dried to give a substantially colorless or slightly colored pyridine-carboxylic acid lactone represented by the formula (I) wherein $R_4$ is a group —N-H—CO—X in high yield.

Now, the process for preparing the color former of the present invention, i.e., lactone color formers of pyridine-carboxylic acid will be illustrated by the following Preparation Examples.

PREPARATION EXAMPLE 1

10 g of quinolinic anhydride and 26 g of N,N-diethyl-m-phenetidine were added to 100 ml of benzene, and 27 g of anhydrous aluminum chloride was added to the mixture in small portions over about 20 minutes while stirring and maintaining the temperature at 30° to 35°C.

Upon completion of the addition, the mixture was allowed to react for 4 hours at a temperature in the range of from 35° to 38°C and thereafter was cooled to room temperature. The benzene was removed by decantation, and the resulting reaction product was added to 300 ml of ice-water followed by stirring. The precipitated solid was filtered, washed with water and dried to give 15.5 g of an isomer mixture comprising 3-[2'-ethoxy-4'-diethylamino-benzoyl]-pyridine-carboxylic acid-(2) and 2-[2'-ethoxy-4'-diethylamino-benzoyl]-pyridine-carboxylic acid-(3) as pale brown crystals having a melting point of 245° to 253°C. 15.5 g of the resulting crystals was then dissolved in dilute aqueous sodium hydroxide. Dilute aqueous hydrochloric acid was added to the solution to adjust the pH to 6 and the precipitated solid was filtered (the filtrate was set aside), washed and dried to give 10 g of an isomer mixture comprising predominantly 3-[2'-ethoxy-4'-diethylamino-benzoyl]-pyridine-carboxylic acid-(2) and a small amount of 2-[2'-ethoxy-4'-diethylamino-benzoyl]-pyridine-carboxylic acid-(3) as light yellowish brown crystals having a melting point of 293° to 297°C. 10 g of the resulting crystals was then recrystallized several times from a mixed solvent of methanol-benzene (1 : 1 by volume) to give 6.5 g of a highly purified 3-[2'-ethoxy-4'-diethylamino-benzoyl]-pyridine-carboxylic acid-(2) as pale yellow crystals having a melting point of 297° to 298°C.

The filtrate having a pH of 6 obtained from the filtration of the above product was then adjusted to a pH of about 2 with dilute aqueous hydrochloric acid, and the precipitated solid was filtered, washed with water and dried to give 4 g of an isomer mixture comprising predominantly 2-[2'-ethoxy-4'-diethylamino-benzoyl]-pyridine-carboxylic acid-(3) and a small amount of 3-[2'-ethoxy-4'-diethylamino-benzoyl]-pyridine-carboxylic acid-(2) as pale brown crystals having a melting point of 176° to 181°C.

4 g of the isomer mixture thus obtained was then recrystallized several times from a mixed solvent of methanoltoluene (1 : 1 by volume) to give 2.3 g of a highly purified 2-[2'-ethoxy-4'-diethylamino-benzoyl]-pyridine-carboxylic acid-(3) as substantially colorless crystals having a melting point of 179° to 180°C.

2 g of the above obtained 3-[2'-ethoxy-4'-diethylamino-benzoyl]-pyridine-carboxylic acid-(2) (m.p., 297° – 298°C) and 1.2 g of 5-dimethylamino-2-naphthol were added to 18.4 g of 95% sulfuric acid, and the mixture was allowed to react at a temperature of 95° to 100°C for 4 hours followed by allowing the mixture to cool to room temperature. The reaction product was then poured into 100 ml of ice-water, and the mixture was adjusted to a pH of about 11 with dilute aqueous sodium hydroxide. 50 ml of benzene was then added to the resulting aqueous solution to transfer the resulting lactone of pyridine-carboxylic acid to the benzene layer which was then recovered by separation. The benzene was distilled off from the benzene layer, and the residue thus obtained was washed successively with water and a small amount of petroleum ether and dried to give 2.3 g of a lactone color former of 3-[3'-diethylamino-7'-dimethylamino-benz(c)-11'-oxy-xanthenyl]-pyridine-carboxylic acid-(2) (Color Former No. 1) as pale brown-colored crystals having a melting point of 217° to 219°C.

2.0 g of 2-[2'-ethoxy-4'-diethylamino-benzoyl]-pyridine-carboxylic acid-(3) (m.p., 179° – 180°C) obtained above and 1.2 g of 5-dimethylamino-2-naphthol were added to 18.4 g of 95% sulfuric acid, and the mixture was allowed to react at a temperature of from 95° to 100°C for 4 hours followed by cooling to room temperature. The reaction product was poured into 100 ml of ice-water and the mixture was adjusted to a pH of about 11 with dilute aqueous sodium hydroxide while stirring, and 50 ml of benzene was added to the mixture to transfer the resulting lactone of pyridine-carboxylic acid to the benzene layer which was then recovered by separation. The benzene was distilled off from the benzene layer, and the residue thus obtained was washed successively with water and a small amount of petroleum ether and dried to give 2.2 g of 2-[3'-diethylamino-7'-dimethylamino-benz(c)-11'-oxy-xanthenyl]-pyridine-carboxylic acid-(3) lactone (Color Former No. 2) as pale brown colored crystals having a melting point of 174° to 176°C.

PREPARATION EXAMPLE 2

4.0 g of the isomer mixture of benzoyl-pyridine-carboxylic acid having a melting point of 245° to 253°C as described in Preparation Example 1 and 2.0 g of 2-naphthol were added to 40 g of 98% sulfuric acid, and the mixture was allowed to react at a temperature of from 95° to 100°C for 4 hours followed by cooling to room temperature. The reaction product was poured into 200 ml of ice-water, and the mixture was adjusted to a pH of about 11 with dilute aqueous sodium hydroxide. To the mixture was added 100 ml of toluene to transfer the resulting lactone of pyridine-carboxylic acid to the toluene layer, and the toluene layer was recovered by separation. The toluene was distilled off from the toluene layer and the residue thus obtained was washed successively with water and a small amount of petroleum ether and dried to give 2.8 g of a mixture comprising 3-[3'-diethylamino-benz(c)-11'-oxyxanthenyl]-pyridine-carboxylic acid-(2 ) lactone and 2-[3'-diethylamino-benz(c)-11'-oxy-xanthenyl]-pyridine-carboxylic acid-(3) lactone (Color Former No. 3) as pale purplish brown-colored crystals having a melting point of 155° to 159°C.

PREPARATION EXAMPLE 3

3.1 g of the isomer mixture of benzoyl-pyridine-carboxylic acid having a melting point of 245° to 253°C as described in Preparation Example 1 and 1.6 g of 5-propionamide-2-naphthol were added to 30 g of 95% sulfuric acid, and the mixture was allowed to react at a temperature of from 95° to 100°C for 5 hours followed by cooling to room temperature. After cooling, the reaction product was worked up in the same manner as described in Preparation Example 2 to give 3.7 g of an isomer mixture comprising 3-[3'-diethylamino-7'-propionamido-benz(c)-11'-oxy-xanthenyl]-pyridine-carboxylic acid-(2) lactone and 2-[3'-diethylamino-7'-propionamido-benz(c)-11'-oxy-xanthenyl]-pyridine-carboxylic acid-(3) lactone (Color Former No. 4) as pale brown colored crystals having a melting point of 231° to 236°C.

PREPARATION EXAMPLE 4

3.1 g of the isomer mixture of benzoyl-pyridine-carboxylic acid having a melting point of 245° to 253°C as described in Preparation Example 1 and 2.6 g of 5-amino-2-naphthol were added to 30 g of 95% sulfuric acid, and the mixture was allowed to react at a temperature of from 90° to 95°C for 5 hours followed by cooling to room temperature. After cooling, the reaction product was worked up in the same manner as described in Preparation Example 2 to give 3.7 g of an isomer mixture comprising 3-[3'-diethylamino-7'-amino-benz(c)-11'-oxy-xanthenyl]-pyridine-carboxylic acid-(2) lactone and 2-[3'-diethylamino-7'-aminobenz(c)-11'-oxy-xanthenyl]-pyridine-carboxylic acid-(3) lactone (Color Former No. 5) as pale green-colored crystals having a melting point of 239° to 242°C.

2.5 g of the above obtained isomer mixture of lactones was dissolved in a mixture of 50 ml of benzene and 0.7 g of triethylamine. 1.2 g of 4-toluoyl chloride was added to the resulting mixture and the mixture was allowed to react at a temperature of 65° to 70°C for 5 hours followed by cooling to room temperature. The reaction product was washed with 50 ml of ice-water, and benzene was distilled off. The residue was washed with a small amount of petroleum ether and dried to obtain 3.2 g of an isomer mixture comprising 3-[3'-diethylamino-7'-(4''-methyl)-benzamide-benz(c)-11'-oxy-xanthenyl]-pyridine-carboxylic acid-(2) lactone and 2-[3'-diethylamino-7'-(4''-methyl)-benzamide-benz(c)-11'-oxy-xanthenyl]-pyridine-carboxylic acid-(3) lactone (Color Former No. 6) as pale reddish purple-colored crystals.

PREPARATION EXAMPLE 5

1. Each of the quinolinic anhydrides (II) and each of the anilins (III) which correspond to the color formers were reacted in the same manner as described in Preparation Example 1 to prepare an isomer mixture of benzoyl-pyridine-carboxylic acid (IV). The resulting isomer mixture was reacted with the corresponding naphthalene compound (V) and the reaction product was worked up in the same manner as described in Preparation Example 2 to obtain an isomer mixture of pyridine-carboxylic acid lactones (Color Former Nos. 7–58) as substantially colorless or slightly colored crystals, respectively.

2. Each of the isomer mixtures of pyridine-carboxylic acid lactones (I, wherein $R_4$ is an amino group) was reacted with an acid halide (VI) and the reaction product was worked up in the same manner as described in Preparation Example 4 to obtain an isomer mixture of pyridine-carboxylic acid lactones (Color Former Nos. 59–75) as substantially colorless or slightly colored crystals, respectively.

The melting points and crystal appearance of the thus obtained color formers, and pyridine-carboxylic acids, naphthalene compounds, and acid halides which were used in this example are shown in Table 1 below.

TABLE 1

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
| --- | --- | --- | --- | --- | --- |
| No. 1 | 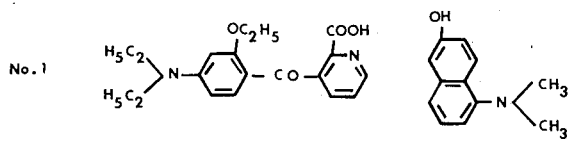 | 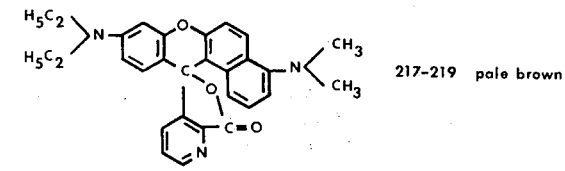 |  | 217–219 | pale brown |

TABLE 1—Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 2 | [structure] | [structure] | [structure] | 174-176 | pale brown |
| No. 3 | [structure] and [structure] | [structure] | [structure] and [structure] | 155-159 | pale purplish brown |
| No. 4 | [structure] and [structure] | [structure] | [structure] and [structure] | 231-236 | pale brown |
| No. 5 | [structure] and [structure] | [structure] | [structure] and [structure] | 239-242 | pale green |
| No. 7 | [structure] and [structure] | [structure] | [structure] and [structure] | 139-143 | pale pink |

TABLE 1—Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 8 | (structure) and (structure) | (structure) | (structure) and (structure) | 172–175 | pale pink |
| No. 9 | (structure) and (structure) | (structure) | (structure) and (structure) | 181–188 | pale pink |
| No. 10 | (structure) and (structure) | (structure) | (structure) and (structure) | 195–203 | pale purple |
| No. 11 | (structure) and (structure) | (structure) | (structure) and (structure) | 172–177 | pale blue |

TABLE 1—Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No.12 | (structure) and (structure) | (structure) | (structure) and (structure) | 198–204 | pale brown |
| No.13 | (structure) and (structure) | (structure) | (structure) and (structure) | 153–160 | pale purple |
| No.14 | (structure) and (structure) | (structure) | (structure) and (structure) | — | pale purple |
| No.15 | (structure) and (structure) | (structure) | (structure) and (structure) | 184–191 | pale brown |

TABLE 1 — Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 16 | *(structures)* and *(structures)* | *(1-naphthol)* | *(structures)* and *(structures)* | 226–230 | pale pink |
| No. 17 | *(structures)* and *(structures)* | *(structure)* | *(structures)* and *(structures)* | 214–219 | pale brown |
| No. 18 | *(structures)* and *(structures)* | *(structure)* | *(structures)* and *(structures)* | 237–243 | pale yellowish |
| No. 19 | *(structures)* and *(structures)* | *(structure)* | *(structures)* and *(structures)* | 186–192 | pale brown |

TABLE 1—Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 20 | [structure] and [structure] | [structure] | [structures] | 224–231 | pale yellowish brown |
| No. 21 | [structure] and [structure] | [structure] | [structures] | 173–178 | pale brown |
| No. 22 | [structure] and [structure] | [structure] | [structures] | — | pale yellowish green |
| No. 23 | [structure] and [structure] | [structure] | [structures] | 162–169 | pale pink |

TABLE I—Continued
| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 24 | 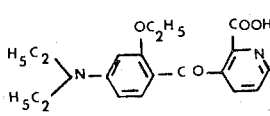 and 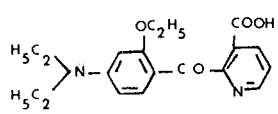 | 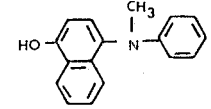 | 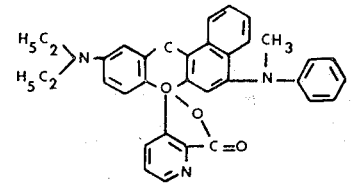 and 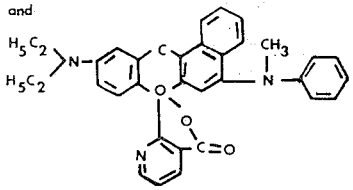 | 154–161 | pale green |
| No. 25 | 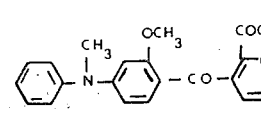 and 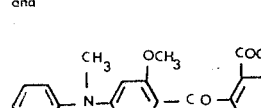 | 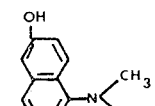 | 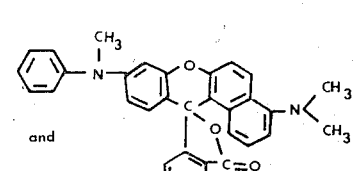 and 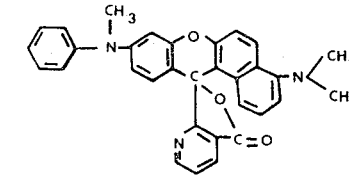 | 183–190 | pale purple |
| No. 26 | 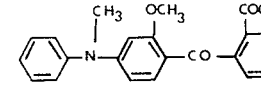 and 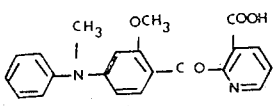 | 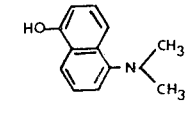 | 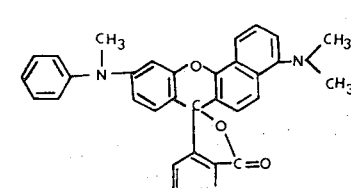 and 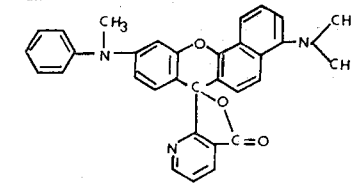 | 194–199 | pale brown |
| No. 27 | 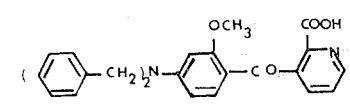 and 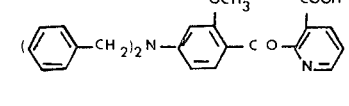 | 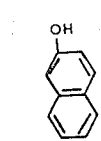 | 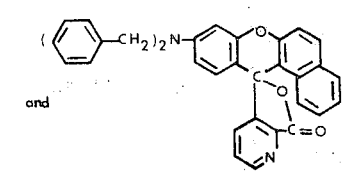 and 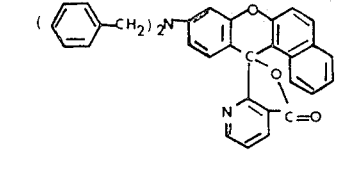 | 167–172 | pale pink |

TABLE 1—Continued
| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 28 | 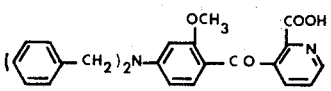 and  | 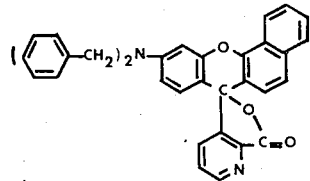 | and 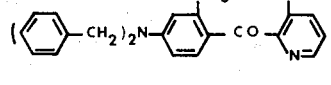 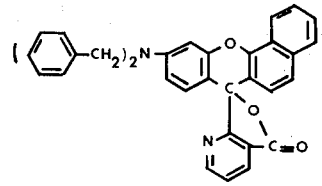 | 230–238 | pale pink |
| No. 29 | 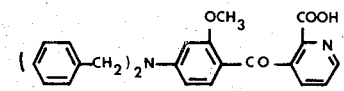 and 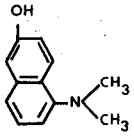 | 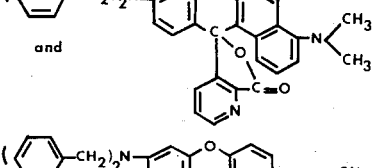 | and 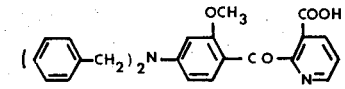 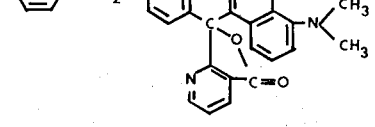 | 174–179 | pale purple |
| No. 30 | 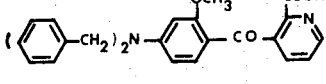 and 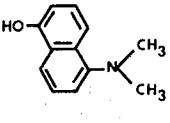 | 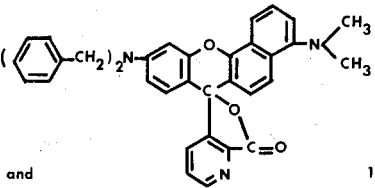 | and 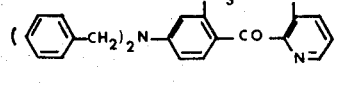 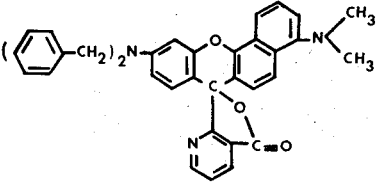 | 193–201 | pale brown |
| No. 31 | 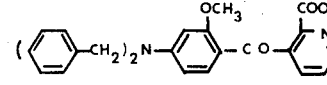 and 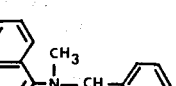 | 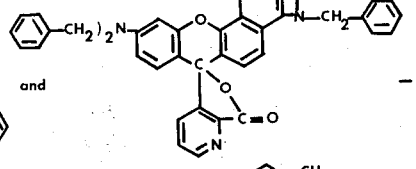 | and 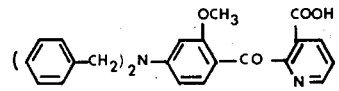 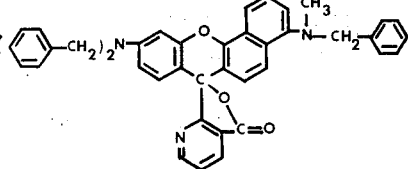 | — | pale brown |

TABLE 1—Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 32 | (structure) and (structure) | (structure) | (structure) and (structure) | — | pale pink |
| No. 33 | (structure) and (structure) | (structure) | (structure) and (structure) | — | pale pink |
| No. 34 | (structure) and (structure) | (structure) | (structure) and (structure) | — | pale brown |
| No. 35 | (structure) and (structure) | (structure) | (structure) and (structure) | — | pale purple |

TABLE 1—Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 36 | (structures) | (structure) | (structures) | — | pale purple |
| No. 37 | (structures) | (structure) | (structures) | — | — |
| No. 38 | (structure) | (structure) | (structure) | 253–256 | pale green |
| No. 39 | (structure) | (structure) | (structure) | 218–221 | pale green |
| No. 40 | (structures) | (structure) | (structures) | 231–236 | pale pink |

TABLE I—Continued
| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 43 | | | | 211–215 | pale ocher |
| No. 44 | | | | 263–266 | pale brown |
| No. 45 | | | | — | pale pink |
| No. 46 | | | | 192–199 | pale brown |
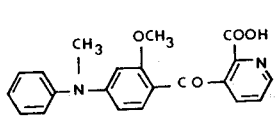

TABLE I – Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 47 | (structures) | (structure) | (structures) | 226–231 | pale pink |
| No. 48 | (structures) | (structure) | (structures) | 239–243 | pale pink |
| No. 49 | (structures) | (structure) | (structures) | 186–00 | pale pink |
| No. 50 | (structures) | (structure) | (structures) | 214–217 | pale purple |

TABLE 1—Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 51 | [structure] and [structure] | [structure] | and [structures] | — | pale green |
| No. 52 | [structure] and [structure] | [structure] | and [structures] | — | pale pink |
| No. 53 | [structure] and [structure] | [structure] | and [structures] | — | pale pink |
| No. 54 | [structure] and [structure] | [structure] | and [structures] | — | pale pink |

TABLE 1—Continued
| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 55 | 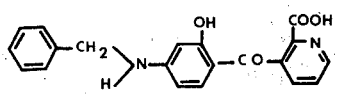 | 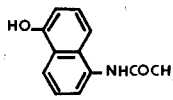 | 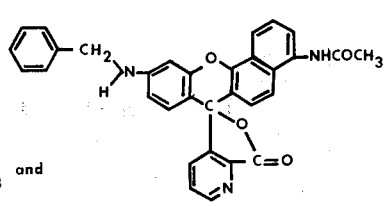 | — | pale brown |
| No. 56 | 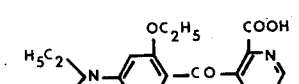 | 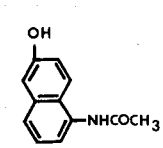 | 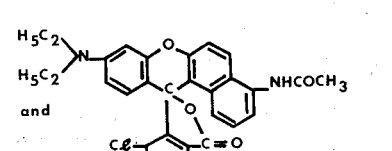 | — | pale pink |
| No. 57 | 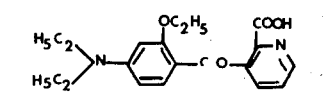 | 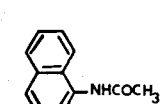 | 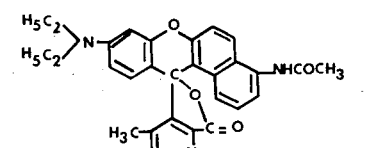 | — | pale pink |
| No. 58 | 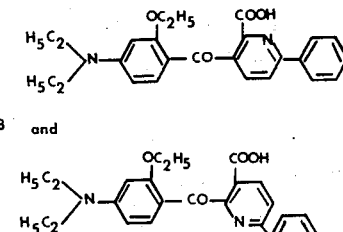 | 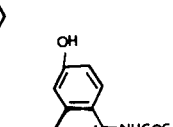 | 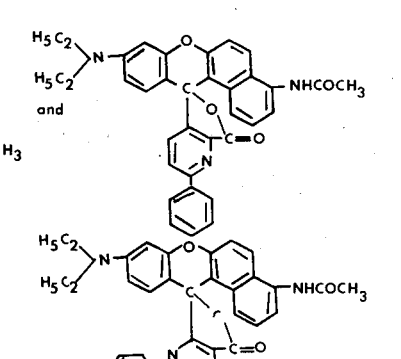 | — | pale brown |

TABLE I—Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 59 | and | CH₂=CH-COCl | and | — | pale brown |
| No. 60 | and | ⌬-COCl | and | 165–169 | pale pink |
| No. 61 | and | (2,5-dimethyl)-COCl | and | — | pale pink |
| No. 62 | and | (o-OCH₃)-COCl | and | 152–155 | pale pink |

TABLE 1—Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 63 | [structure] and [structure] | [structure] | and [structure] | 136-159 | pale pink |
| No. 64 | [structure] and [structure] | [structure] | and [structure] | — | pale reddish purple |
| No. 65 | [structure] and [structure] | [structure] | and [structure] | 171-174 | pale yellow |
| No. 66 | [structure] and [structure] | [structure] | and [structure] | 163-167 | pale pink |

TABLE I – Continued
| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 67 | 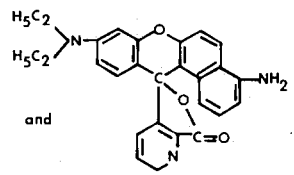 | 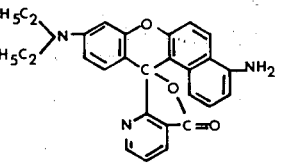 | 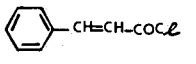 | 218–225 | pale brown |
| No. 68 | 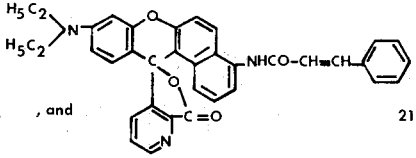 | 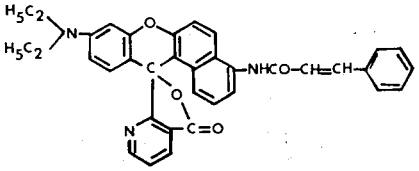 | 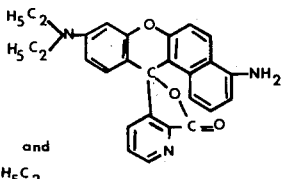 | – | pale brown |
| No. 69 | 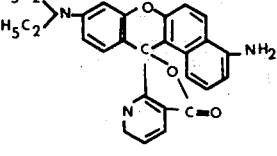 | 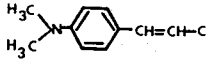 |  | – | pale pink |
| No. 70 | 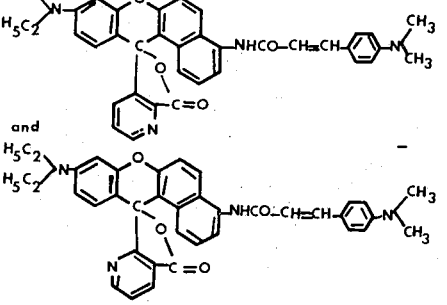 | $CH_3COCl$ | 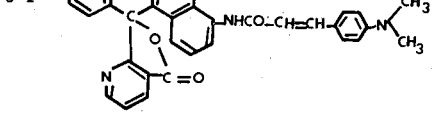 | 248–254 | pale purple |

TABLE 1—Continued
| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 71 | 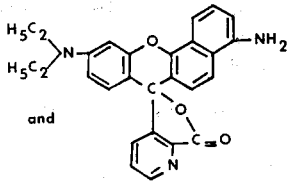 | 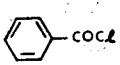 | 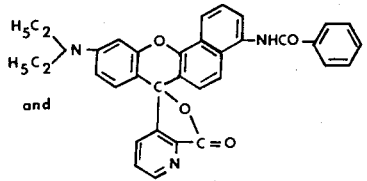 | 158-161 | pale pink |
| No. 72 | 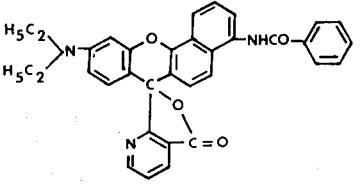 | 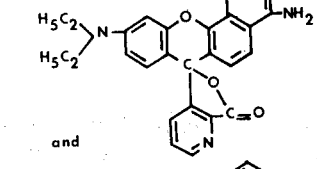 |  | 163-166 | pale pink |
| No. 73 | 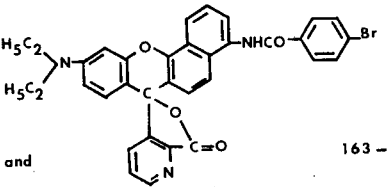 | 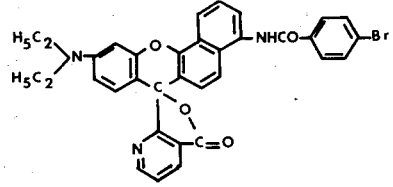 | 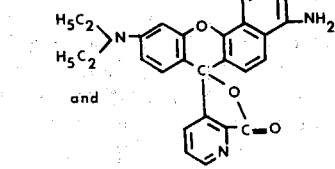 | 241-249 | pale brown |

TABLE 1—Continued

| Color Former | Benzoyl-Pyridine-Carboxylic Acid Represented by the Formula (IV) | Naphthalene Compound Represented by the Formula (V) | Lactone Color Former Represented by the Formula (I) | Melting Point (°C) | Crystal Appearance |
|---|---|---|---|---|---|
| No. 74 | (structure) and (structure) | CH₃COCl | (structure) and (structure) | 246–253 | whitish green |
| No. 75 | (structure) and (structure) | (structure with CH₃, COCl, Cl) | (structure) and (structure) | 183–187 | pale pink |

The processes for producing pressure-sensitive copying papers using pyridine-carboxylic acid lactones represented by the formula (I) as a color former are well known in the art and include the method in which phenomenon of complex coacervation is utilized to produce microcapsules as disclosed in U.S. Pat. Nos. 2,800,457 and 2,800,458, the interfacial polymerization method as disclosed in Japanese Pat. Publication Nos. 446/1967 and 771/1967 and the internal polymerization method as described in applicants' co-pending Japanese Pat. Application Nos. 38087/1968 and 69448/1969. The color former is generally used in an amount of from about 0.5 to 5% by weight based on the previously described organic solvent such as ethylene glycol, chlorobenzenes, diphenyl chloride, dibenzylbenzene, dibenzyltoluene, diethylphthalate, trioctyl phosphate, an alkylnaphthalene, naphthylalkyl alcohols, etc.

The pressure-sensitive copying paper using pyridine-carboxylic acid lactones represented by the formula (I) will now be illustrated in greater detail by the following Examples, but they are not to be construed as limiting the scope of this invention. In these examples, all percentages, parts and the like are by weight unless otherwise indicated.

EXAMPLE 1

2.0 Grams of Color Former Nos. 1 and 2 were taken up and treated as follows. Each color former was dissolved in 100 g of dibenzyl toluene, and 20 g of gum arabic and 160 g of water were added thereto at a temperature of 50°C to emulsify. To this emulsion were added 20 g of acid-treated gelatin and 160 g of water and, under stirring, acetic acid was added thereto to adjust the pH to 5. Then, 500 g of water was added thereto to allow coacervation to proceed. Thus, thick, liquid film of gelatin-gum arabic was formed around oil droplets of dibenzyl toluene containing dissolved therein the color former. After adjusting the pH to 4.4, 4 g of a 37% formalin aqueous solution was added thereto to harden the above-described liquid film. Then, the system was cooled to 10°C and, after adding thereto dilute aqueous sodium hydroxide to adjust the pH to 9, it was allowed to stand for 5 to 6 hours to thereby complete encapsulation.

The resulting microcapsule-containing liquid was applied to a paper by a coating method such as roll-coating, air knifecoating, etc. After drying, there was obtained a colorless coated paper (upper sheet paper). When this upper sheet paper was intimately superposed on a lower sheet paper having coated thereon an active clay substance as a color developer and a localized pressure was applied to the assembly by handwriting, a purplish blue color was immediately formed on the lower sheet paper at the pressed area.

There was observed almost no discoloration and fading of the thus developed purplish blue color even when it was exposed directly to sunlight for a long period of time.

Alternatively, when the upper sheet paper was intimately superposed on a lower sheet paper having coated thereon an acidic organic polymer and a localized pressure was applied thereto by handwriting, a purplish blue color was immediately formed on the lower sheet paper at the pressure-applied area.

EXAMPLE 2

2.0 Grams of Color Former No. 3 was taken up and treated in the same manner as described in Example 1. After coating and drying, there was obtained a colorless upper sheet paper.

When this upper sheet paper was intimately superposed on a lower sheet paper having coated thereon an active clay substance as a color developer and a localized pressure was applied thereto by handwriting, there was immediately developed a reddish purple color on the lower sheet paper at the pressed area. There was observed almost no discoloration nor fading of the thus developed reddish purple color even when it was directly exposed to sunlight for a long period of time. Alternatively, when the upper sheet paper was intimately superposed on a lower sheet paper having coated thereto an acidic organic polymer as the color developer and a localized pressure was applied to the assembly by handwriting, there was immediately developed a reddish purple color on the lower sheet paper at the pressed area.

EXAMPLE 3

2.0 Grams of Color Former No. 4 was taken up and treated in the same manner as described in Example 1.

After coating and drying there was obtained a colorless upper sheet paper. The resulting paper was intimately superposed on a lower sheet paper having coated thereon an acidic organic polymer, an acid clay substances or a combination thereof, as a color developer. When a localized pressure was applied to the assembly, a red color was immediately formed on the lower sheet paper at the pressed area. The thus formed red color exhibited a sufficient stability to the lapse of time for practical use.

EXAMPLE 4

2.0 Grams of Color Former Nos. 5 – 75 were taken up and each of them was treated in the same manner as described in Example 1.

After coating and drying, there were obtained colorless upper sheet papers. When each of the resulting papers was intimately superposed on a lower sheet paper having coated thereon an acid clay substance as a color developer and a localized pressure was applied to the assembly by handwriting, there was immediately developed a deep color image on the lower sheet paper at the pressed area. The thus developed color images showed sufficient stability for practical use. The hues developed on the lower sheets are shown in Table 2 below.

Table 2

| Color Former | Hue | Color Former | Hue |
|---|---|---|---|
| No. 5 | purplish blue | No. 6 | red |
| No. 7 | red | No. 8 | red |
| No. 9 | red | No. 10 | reddish purple |
| No. 11 | purplish blue | No. 12 | purplish blue |
| No. 13 | purplish blue | No. 14 | purplish blue |
| No. 15 | reddish purple | No. 16 | reddish purple |
| No. 17 | red | No. 18 | dark reddish brown |
| No. 19 | dark reddish brown | No. 20 | dark green |
| No. 21 | dark reddish brown | No. 22 | dark green |
| No. 23 | green | No. 24 | dark green |
| No. 25 | reddish purple | No. 26 | reddish brown |

Table 2-continued

| Color Former | Hue | Color Former | Hue |
|---|---|---|---|
| No. 27 | red | No. 28 | red |
| No. 29 | purplish blue | No. 30 | dark reddish brown |
| No. 31 | dark reddish brown | No. 32 | red |
| No. 33 | red | No. 34 | red |
| No. 35 | purplish blue | No. 36 | purplish blue |
| No. 37 | purplish blue | No. 38 | reddish purple |
| No. 39 | reddish purple | No. 40 | red |
| No. 41 | red | No. 42 | red |
| No. 43 | reddish purple | No. 44 | reddish purple |
| No. 45 | red | No. 46 | red |
| No. 47 | red | No. 48 | red |
| No. 49 | red | No. 50 | red |
| No. 51 | reddish purple | No. 52 | red |
| No. 53 | red | No. 54 | red |
| No. 55 | red | No. 56 | reddish purple |
| No. 57 | reddish purple | No. 58 | reddish purple |
| No. 59 | reddish purple | No. 60 | reddish purple |
| No. 61 | reddish purple | No. 62 | reddish purple |
| No. 63 | reddish purple | No. 64 | reddish purple |
| No. 65 | reddish purple | No. 66 | reddish purple |
| No. 67 | reddish purple | No. 68 | reddish purple |
| No. 69 | reddish purple | No. 70 | red |
| No. 71 | red | No. 72 | red |
| No. 73 | red | No. 74 | reddish brown |
| No. 75 | reddish brown | | |

EXAMPLE 5

2.4 Grams of Color Former No. 24, 0.3 g of o-hydroxybenzalacetophenone, 0.1 g of rhodamine B-anilinolactam, 0.1 g of malachite green lactone and 0.1 g of benzoyl leuco methyleneblue were treated and coated in the same manner as described in Example 1 to prepare an upper sheet paper. When this upper sheet paper was superposed on a lower sheet paper having coated thereon an active clay substance as a color developer and a localized pressure was applied to the assembly by handwriting, there was immediately developed a black color on the lower sheet paper. The thus developed black color scarcely underwent change in hue and fading.

EXAMPLE 6

2.0 g of Color Former No. 1 was dissolved in 50 g of diisopropyl biphenyl, and a solution comprising 10 g of toluylene diisocyanate, 6 g of bisphenol A, 0.5 g of zinc octylate and 20 g of methylene chloride was added thereto to prepare a first solution.

10 g of gum arabic was dissolved in 50 g of water at 30°C, and the above first solution was added thereto followed by emulsifying using a homogenizer to prepare an oil-in-water emulsion having a particle size of 10 to 15 μ.

The thus obtained emulsion was poured into 200 g of warm water at 50°C, and the temperature was elevated to 80°C while stirring. The reaction system was maintained at that temperature for 30 minutes to polymerize toluylene diisocyanate and bisphenol A around the surface of oil droplets to form a capsule wall. After completion of encapsulation, the resulting microcapsule-containing liquid was applied onto a paper with an air knife followed by drying. An active clay substance was further coated thereon followed by drying thereby obtaining a single recording paper. When a localized pressure was applied directly to the coating layer by typewriting or handwriting, a distinct purplish blue-colored image was formed at the pressed area.

While the invention has been described in detail and with reference to specific embodiments thereof, it will be apparent to one skilled in the art that various changes and modifications can be made without departing from the spirit and scope thereof.

What is claimed is:

1. A pressure-sensitive copying paper system comprising an adsorbent solid acid and a micro-encapsulated color former capable of forming a distinct color when reacted with said adsorbent solid acid, each coated on the same or different surfaces of one or more supports, said microcapsules containing an organic solvent having dissolved therein a lactone color former comprising at least one lactone compound derived from pyridine-carboxylic acid represented by the formula

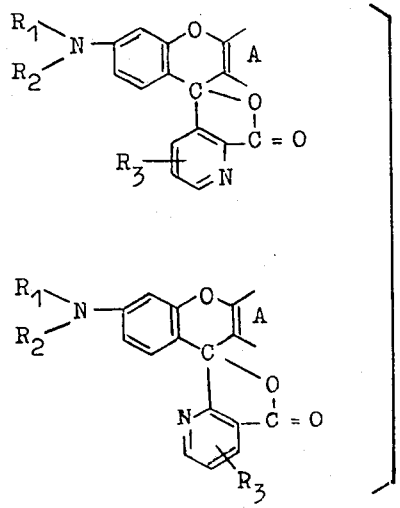

(I)

or a mixture thereof, wherein $R_1$ represents a hydrogen atom, a lower alkyl group or a benzyl group; $R_2$ represents a lower alkyl group, a benzyl group or a substituted or unsubstituted phenyl group wherein the substituent is a lower alkyl group or a halogen atom; $R_3$ represents a hydrogen atom, a lower alkyl group, a halogen atom or a phenyl group; and the partial structure

represents

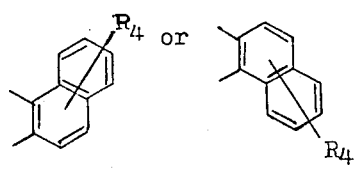

wherein $R_4$ represents a hydrogen atom, a lower alkyl group, a lower alkoxy group, a halogen atom, an amino, mono-lower alkylamino, di-lower alkyl-amino, monobenzylamino, dibenzylamino, N-lower alkyl-N-benzylamino, anilino, N-lower alkylanilino or -NHCO-X group wherein X represents a lower alkyl, lower alkenyl or a substituted or unsubstituted styryl, phenyl or naphthyl group, the substituent being a lower alkyl, lower alkoxy, di-lower alkylamino, hydroxy or nitro group or a halogen atom, wherein the lower alkyl, alkoxy and alkenyl groups have 1 to 5 carbon atoms.

2. The pressure sensitive copying paper system of claim 1, wherein said color former is a mixture of the following compounds:

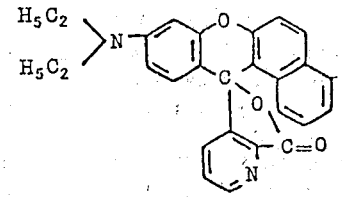

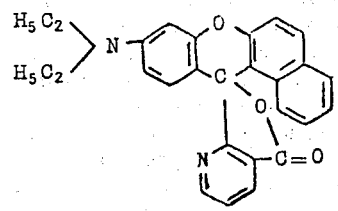

3. The pressure sensitive copying paper system of claim 1, wherein said color former is selected from the group consisting of:

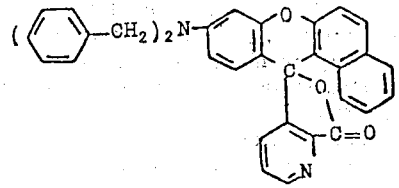

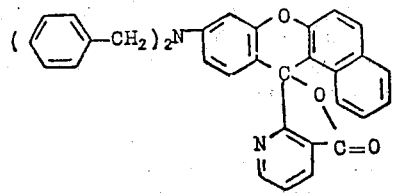

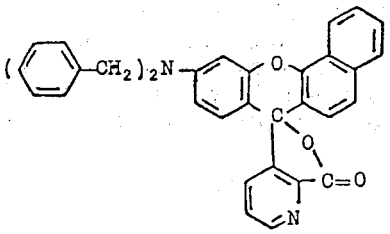

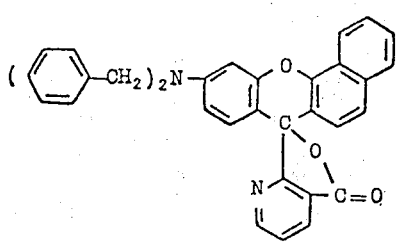

4. The pressure sensitive copying paper system of claim 1, wherein said color former is selected from the group consisting of:

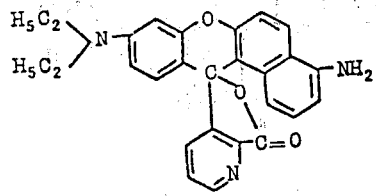

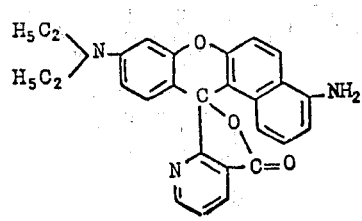

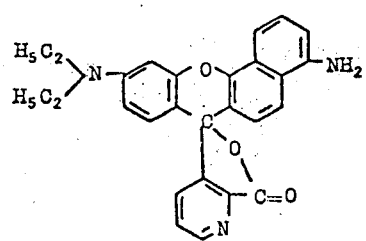

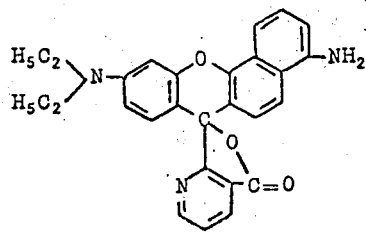

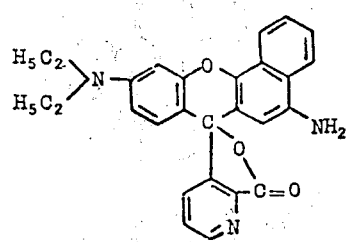

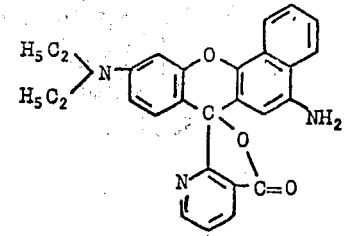

5. The pressure sensitive copying paper system of claim 1, wherein said color former is selected from the group consisting of:

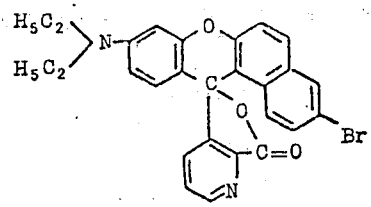

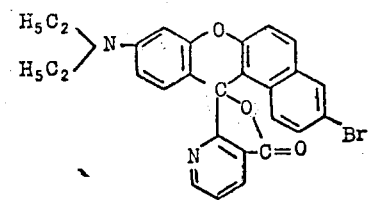

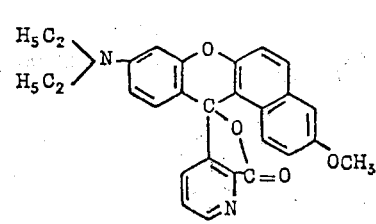

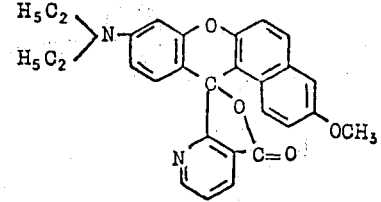

6. The pressure sensitive copying paper system of claim 1, wherein said color former is selected from the group consisting of:

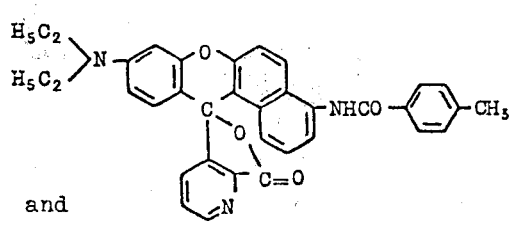

and

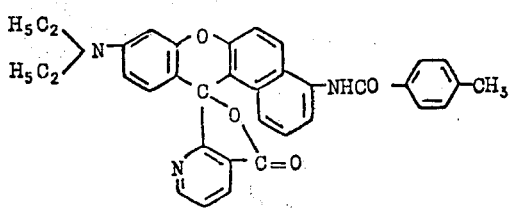

7. The pressure sensitive copying paper system of claim 1, wherein said color former is selected from the group consisting of:

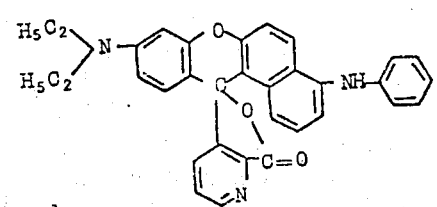
and
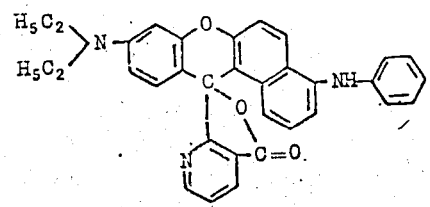
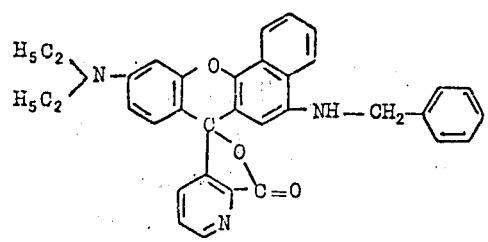
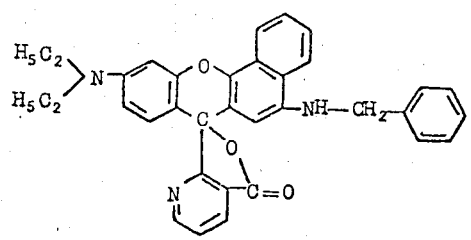
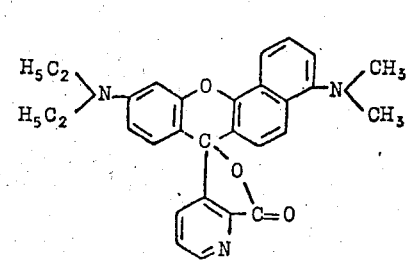
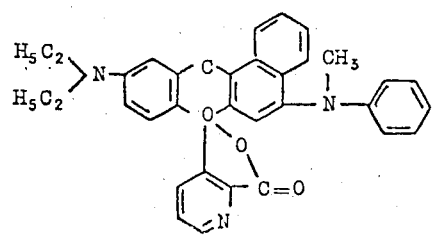
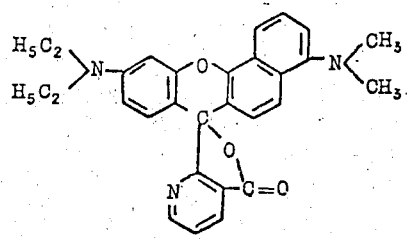
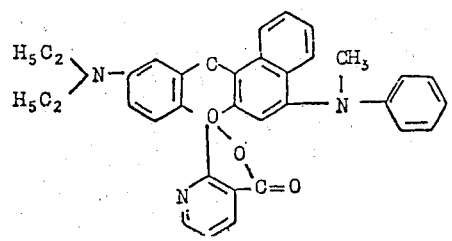
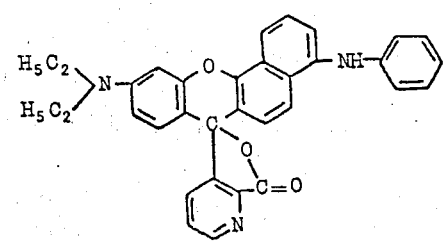
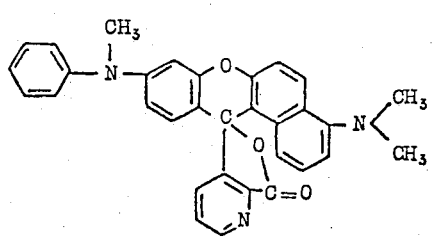
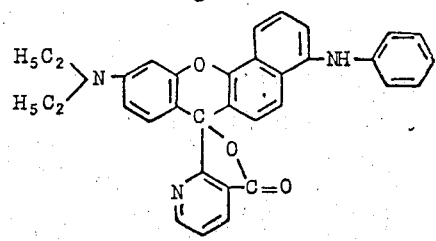
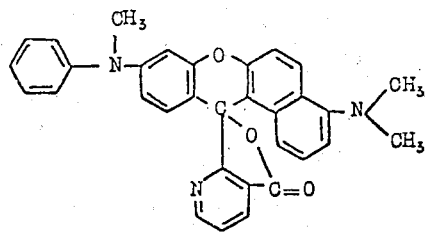

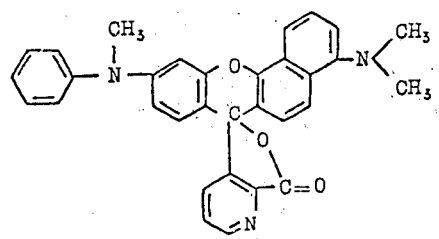
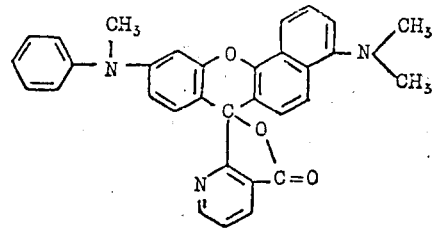
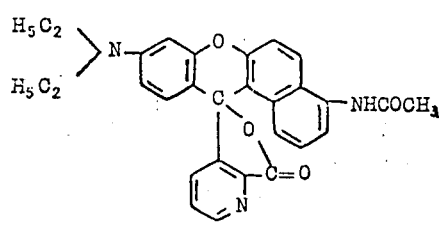
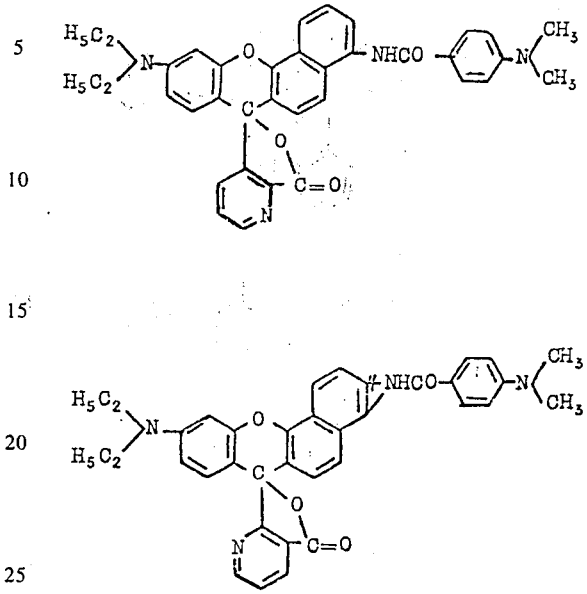
* * * * *